United States Patent
Zhang et al.

(10) Patent No.: US 10,222,311 B2
(45) Date of Patent: Mar. 5, 2019

(54) METHOD FOR EVALUATING AEROSOL MASS OF ELECTRONIC CIGARETTE

(71) Applicant: CHINA TOBACCO YUNNAN INDUSTRIAL CO., LTD, Kunming (CN)

(72) Inventors: Xia Zhang, Kunming (CN); Yi Han, Kunming (CN); Donglai Zhu, Kunming (CN); Shoubo Li, Kunming (CN); Xiaowei Gong, Kunming (CN); Ping Lei, Kunming (CN); Shanzhai Shang, Kunming (CN); Yongkuan Chen, Kunming (CN); Liu Yang, Kunming (CN); Zhiyong Sun, Kunming (CN)

(73) Assignee: CHINA TOBACCO YUNNAN INDUSTRIAL CO., LTD, Kunming (CN)

( * ) Notice: Subject to any disclaimer, the term of this patent is extended or adjusted under 35 U.S.C. 154(b) by 0 days.

(21) Appl. No.: 14/784,552

(22) PCT Filed: Nov. 10, 2014

(86) PCT No.: PCT/CN2014/090730
§ 371 (c)(1),
(2) Date: Oct. 14, 2015

(87) PCT Pub. No.: WO2016/019648
PCT Pub. Date: Feb. 11, 2016

(65) Prior Publication Data
US 2017/0167963 A1    Jun. 15, 2017

(30) Foreign Application Priority Data
Aug. 5, 2014 (CN) .......................... 2014 1 0380290

(51) Int. Cl.
*G01N 15/00* (2006.01)
*A24F 47/00* (2006.01)
*G01N 15/06* (2006.01)
*G01N 15/02* (2006.01)

(52) U.S. Cl.
CPC ....... *G01N 15/0656* (2013.01); *A24F 47/008* (2013.01); *G01N 15/0266* (2013.01); *G01N 2015/0003* (2013.01); *G01N 2015/0026* (2013.01)

(58) Field of Classification Search
CPC .......................... G01N 15/0656; A24F 47/008
USPC ............................................ 702/26; 424/450
See application file for complete search history.

(56) References Cited

U.S. PATENT DOCUMENTS

| | | | | |
|---|---|---|---|---|
| 5,681,752 A * | 10/1997 | Prather | ............... | H01J 49/0022 250/281 |
| 7,111,496 B1 * | 9/2006 | Lilienfeld | .............. | G01N 21/51 356/338 |
| 2003/0016357 A1 * | 1/2003 | Shofner | ............. | G01N 15/0211 356/337 |
| 2003/0062042 A1 * | 4/2003 | Wensley | ................ | A61K 9/007 128/203.12 |
| 2008/0138399 A1 * | 6/2008 | Gonda | .................. | A24F 47/002 424/450 |
| 2009/0084979 A1 * | 4/2009 | DeWalch | ................ | C40B 60/10 250/458.1 |
| 2012/0096924 A1 * | 4/2012 | Olfert | ................ | G01N 15/0255 73/28.01 |
| 2014/0178461 A1 * | 6/2014 | Rigas | .................. | A61K 31/661 424/450 |

* cited by examiner

*Primary Examiner* — Eman A Alkafawi
(74) *Attorney, Agent, or Firm* — Gokalp Bayramoglu

(57) ABSTRACT

The invention discloses a method for evaluating the aerosol mass of electronic cigarettes, comprising the following steps: (1) Measurement: an electronic cigarette is smoked to measure the particle size distribution and the particle numbers in the generated aerosol, and measure the volume flow rate C of the aerosol and the testing time t; (2) Data processing: based on the particle size distribution and number, the aerosol particles are classified with classifying diameter $d_i$, and the corresponding average number concentrations n of the particles to classifying diameters $d_i$ are calculated; and (3) the generated aerosol mass is calculated according to the calculation formula for the aerosol mass of the invention.

3 Claims, No Drawings ns of the aerosol mass of electronic cigarettes are mainly based on human visual sensory evaluation, which can bring multiple subjective uncertainties. So far, the objective evaluation methods of the aerosol mass of electronic cigarettes have not been reported.

METHOD FOR EVALUATING AEROSOL MASS OF ELECTRONIC CIGARETTE

CROSS-REFERENCE TO RELATED APPLICATIONS

This application is a 371 of PCT/CN2014/090730 filed Nov. 10, 2014 which claims benefit of CN 201410380290.7 filed on Aug. 5, 2014, both of which are incorporated herein by reference in their entireties.

FIELD OF THE INVENTION

The invention relates to a method for evaluating aerosol mass of electronic cigarettes.

BACKGROUND OF THE INVENTION

Electronic cigarettes are electronic devices for delivering nicotine to the respiratory system by means of electronic heating, and it vaporizes a nicotine-containing solution to generate an aerosol. As compared with conventional cigarettes, the electronic cigarette has the following advantages: (a) the aerosol of the electronic cigarette does not contain harmful ingredients, such as tar, CO, and HCN; (b) the electronic cigarette vaporize a nicotine-containing solution (abbreviate as "e-liquid") to generate an aerosol, and the aerosol can be quickly diluted in air, thereby no formation of second-hand smoke; (c) the use of the electronic cigarette does not involve a combustion process, and thus no cigarette ash and cigarette butt are produced, thereby to avoid potential danger of fire hazard. Such an electronic cigarette which combines modern microelectronic technique, biological technique, and healthy lifestyle concept together, can firmly grasp the mentality of consumers, and attract numerous consumers in a short time. At present, researches to the electronic cigarettes primarily focus on the design of electronic cigarette article, e-liquid and relevant accessories.

The aerosol mass is an important quality index for evaluating the performances of an electronic cigarette. The majority of smoke ingredients of conventional cigarettes is solid particles, and the minority of the smoke ingredients is liquid particles. Particles in the smoke have a large volume, and the aerosol mass of conventional cigarettes is usually measured by using a light scattering method, for example, see Chinese patent CN1113620C. The primary mechanism of the light scattering method is described as follows: a beam of light having a specific wavelength passes through smoke aerosol, the more solid particles in the smoke, the stronger scattering actions on light, whereby the transmission intensity of the light is lower; thus, the mass of the solid particles in the smoke can be measured quantitatively by measuring the transmission intensity of the light. However, the primary constituent of the electronic cigarette solution is liquid, such as propylene glycol, glycerol, nicotine, and flavor, and they are readily vaporizable upon heating to form small droplets which are dispersed in air, thereby to form an aerosol. The droplet particles not only have a smaller volume than solid particles, and more importantly, the droplets per se are transparent so that they do not have significant scattering actions on light as those of solid particles. Hence, when the light scattering method is used to measure the aerosol mass of electronic cigarettes, the corresponding scattering intensity and measuring precisions are low and the reproducibility is poor. Therefore, devices and methods for evaluating the aerosol mass of conventional cigarettes are not suitable for aerosol mass of electronic cigarettes. At present, the evaluations to the aerosol mass of electronic cigarettes are mainly based on human visual sensory evaluation, which can bring multiple subjective uncertainties. So far, the objective evaluation methods of the aerosol mass of electronic cigarettes have not been reported.

SUMMARY OF THE INVENTION

To solve the disadvantageous of existing evaluation methods, the object of this invention is providing a novel method of evaluating the aerosol mass of electronic cigarettes, which can fill up technical blanks of the objective evaluation methods of the aerosol mass of electronic cigarettes. The method can make precise objective evaluations to the aerosol mass of electronic cigarettes, and can avoid errors of existing sensory evaluation methods caused by vision disparity.

The present invention relates to a method for evaluating the aerosol mass of electronic cigarettes, comprising the following steps: (1) Measurement: an electronic cigarette is smoked to measure the particle size distribution and particle numbers in the aerosol, and to measure the volume flow rate C of the aerosol and the testing time t; (2) Data processing: aerosol particles having a diameter range of 4 to 1000 nm are classified with classifying diameter di, the classifying diameter may include 38 grades, being defined as d1 to d38, and the corresponding numerical values of the classifying diameter in the 38 grades are shown as follows: 4.87, 5.62, 6.49, 7.5, 8.66, 10, 11.55, 13.34, 15.4, 17.78, 20.54, 23.71, 27.38, 31.62, 36.52, 42.17, 48.7, 56.23, 64.94, 74.99, 86.6, 100, 115.48, 133.35, 153.99, 177.83, 205.35, 237.14, 273.84, 316.23, 365.17, 421.7, 486.97, 562.34, 649.38, 749.89, 865.96, 1000, with the unit of nm; the corresponding average number concentrations n of the particles to the classifying diameters di are calculated; the so-called "classifying diameter di" is meant to the average diameter of the aerosol particles in each grade when the aerosol particles are classified according to the diameters thereof; (3) Evaluation: assumed that the particles in the aerosol of the electronic cigarette are spherical and the particle density is the standard density ρ0, that is, the water density of 1.0 g/cm3; the aerosol mass is calculated according to the following formula:

$$W = \sum_{i=1}^{38} \left( \frac{1}{6}\pi d_i^3 \times \rho_0 \times 10^{-21} \times n \times \int_{t_0}^{t_1} C dt \right).$$

In the above formula, W denotes the aerosol mass, with the unit of g; $d_i$ denotes the corresponding classifying diameter of the aerosol particles, with the unit of nm; $\rho_0$ is the assumed standard density of the particles, i.e., 1.0 g/cm$^3$; n denotes the corresponding average number concentration of the aerosol particles to the classifying diameter $d_i$, with the unit of/cm$^3$, wherein the n value may be calculated with the measured particle size distribution and the aerosol particle numbers during the measurement (1) and the classifying numbers, for example, the n value can be obtained by using the working software of the Fast Particulate Spectrometer as described in the following text; C denotes the volume flow rate of the aerosol, with the unit of cm$^3$/s; $t_0$ denotes the starting testing time point, and $t_1$ denotes the terminal testing time point, each with the unit of s.

In a preferred embodiment, the Smoking Cycle Simulator (SCS) and the Fast Particulate Spectrometer (DMS500) may be used in combination to accomplish the measurement (1) and the Data processing (2). A whole set of the device is commercially available from British CAMBUSTION, and the smoking of the electronic cigarette is simulated by using the Smoking Cycle Simulator (SCS) while setting suitable parameters, including puff volume, puff profile, puff frequency, body temperature, data collection speed, dilution ratio, etc. The aerosol generated during the smoking is led to the Fast Particulate Spectrometer (DMS500). The Fast Particulate Spectrometer (DMS500) electrifies the aerosol particles by discharge via a charger, and based on the difference in their electrical mobility the Fast Particulate Spectrometer (DMS500) can separate the aerosol particles having different particle sizes. Meanwhile, online and real-time measurements of the particle size distribution and aerosol particle numbers. After the measurement is completed, the initial data which is output by the DMS 500 is processed to acquire the average number concentrations n for per puff of the aerosol particles corresponding to classifying diameters $d_i$, the aerosol flow rate C and the testing time t. Then, the aerosol mass is evaluated by combining relevant references and aerosol theories with the hypothesis that the aerosol particles in the smoke of the electronic cigarette are spherical and the particle density is the standard density, i.e., the water density of 1.0 g/cm$^3$. Essentially, when the differences among the aerosol mass for per puff of the same electronic cigarette and those of different electronic cigarettes are compared, as long the particle density is fixed, resultant relative values will not be influenced. Actually, when the aerosol mass is compared, the density could be randomly selected, and that is, the total mass of the corresponding aerosol particles of classifying diameters is the aerosol mass.

In a preferred embodiment of the invention, the electronic cigarette heats a nicotine-containing solution by means of electrical heating so as to generate an aerosol.

In a preferred embodiment of the invention, the Fast Particulate Spectrometer (DMS500) classifying the diameters of the aerosol particle having a diameter range of 4 to 1000 nm via a classifier. Such a diameter range is selected for the reason that almost all the diameters of the aerosol particles measured by experiments fall into the selected range. Thus, when the total mass of the aerosol particles is measured, the selected diameter range can cover almost all aerosol particles.

The specific calculation formulae are as follows:

(1) The volume of the corresponding particles to classifying diameter:

$$v_i = \frac{1}{6}\pi d_i^3;$$

(2) The mass of the corresponding particles to classifying diameter:

$$m_i = v_i \times \rho_0 \times 10^{-21};$$

(3) The aerosol flow rate:

$$C = C1 + C2;$$

(4) The actual volume of the aerosol:

$$V = \int_{t_0}^{t_1} C dt;$$

(5) The corresponding particle numbers to classifying diameter:

$$N = n \times V;$$

(6) The aerosol mass:

$$W = \sum_{i=1}^{38} (m_i \times N).$$

The mass of the aerosol having a specific volume is used to characterize the aerosol mass W, and it is calculated according to the following formula:

$$W = \sum_{i=1}^{38} \left( \frac{1}{6}\pi d_i^3 \times \rho_0 \times 10^{-21} \times n \times \int_{t_0}^{t_1} C dt \right).$$

In the above formula, W denotes the aerosol mass, with the unit of g; $d_i$ denotes the corresponding classifying diameter of the aerosol particles, including 38 grades (the corresponding numerical values have been described in the preceding text), with the unit of nm; $\rho_0$ is the assumed standard density of the particles, i.e., 1.0 g/cm$^3$; n denotes the average number concentration of the corresponding aerosol particles to the individual classifying diameter $d_i$, with the unit of/cm$^3$; C denotes the volume flow rate of the aerosol, with the unit of cm$^3$/s; $t_0$ denotes the starting testing time point, and $t_1$ denotes the terminal testing time point, each with the unit of s. In the formula (1), $v_i$ is the volume of the corresponding particles to classifying diameter, with the unit of nm$^3$; in the above formula (2), $m_i$ is the mass of the corresponding particles to classifying diameter, with the unit of g; in the formula (3), $C_1$ is a primary dilution flow rate, means the gas volume mixed into the smoke in a unit time period, and $C_2$ is the smoke flow rate, both of them with the unit of cm$^3$/s; after the gas and the smoke are mixing, the total aerosol flow rate may be obtained; in the formula (4), V is an actual aerosol volume as be measured, with the unit of cm$^3$; in the formula (5), N is the particle numbers with different classifying diameter being measured by the device.

Since the smoking of the electronic cigarette is a continuous process, the actual aerosol volume V in the formula (4) is the integral of the aerosol flow rate C in relation to the measuring time t, wherein $t_0$ is the starting testing time point, and $t_1$ is the terminal testing time point. Furthermore, because of the detection signal temporal broadening, the device may make an automatic average to make the actual testing time t longer than the setting smoking duration time. When the testing time is a smoking time for per puff, the calculated aerosol mass is the aerosol mass for per puff of the electronic cigarette.

As compared to the prior art, the invention has the following advantages:

1. As the methods for the objective evaluation of the aerosol mass of electronic cigarette are not reported, the invention fills up the blank in the respect of the objective evaluation of the aerosol mass of the electronic cigarette.

2. At present, the aerosol mass of electronic cigarettes commercially available on the market is evaluated based on human visual sensory evaluation, and thus there are great artificial differences. However, the present invention provides an objective quantitative method for evaluating the aerosol mass of the electronic cigarette, which can be beneficial to monitor the quality of electronic cigarettes.

3. When the conventional light scattering method is applied in the measurement of the aerosol mass of electronic cigarette, both the precision and the reproducibility are poor, while the method of the invention can be applied in the measurement of the aerosol mass of electronic cigarette with high sensitivity, precision and reproducibility.

EMBODIMENTS

The following examples are combined to further describe the present invention, but not limit the invention.

Examples

Two commercially-available electronic cigarette products are selected, being named as the electronic cigarette 1 and the electronic cigarette 2, respectively.

A Smoking Cycle Simulator (SCS) is used to simulate the smoking of the electronic cigarettes 1 and 2, respectively, then, the generated aerosol are analyzed by a Fast Particulate Spectrometer (DMS500), respectively. First, the setting parameters of the SCS and the DMS500 as follows: SCS, puff volume of 55 ml, puff frequency of 30 s, and body temperature of 320 K; DMS, data collection frequency of 10 Hz, a secondary dilution ratio of 300:1. Of cause, other suitable working parameters also can be used. After the parameters are set, the electronic cigarettes are smoked, and each electronic cigarette is smoked for ten puffs. The particle size distribution and particle numbers of the aerosol generated from two electronic cigarettes are online and real-time measured, and at the same time, the aerosol flow rate C and the testing time t are measured. After the measurements are completed, the DMS500 will output a standard data file, and the data file is browsed using Excel, then being processed to acquire the following indexes, corresponding classifying diameters di to the aerosol particles, corresponding average number concentrations n of the aerosol particles to the classifying diameters di. Then, the calculation is made according to the following formula:

$$W = \sum_{i=1}^{38} \left( \frac{1}{6}\pi d_i^3 \times \rho_0 \times 10^{-21} \times n \times \int_{t_0}^{t_1} C\,dt \right)$$

to obtain the aerosol mass for per puff of each electronic cigarette. The experimental results are shown in the following Table 1.

TABLE 1

The data of the aerosol mass of two electronic cigarettes

| Sample No. | The number of smoking puffs | Aerosol mass W, g |
|---|---|---|
| 1 | 1 | $0.976 \times 10^{-3}$ |
|   | 2 | $0.885 \times 10^{-3}$ |
|   | 3 | $0.874 \times 10^{-3}$ |
|   | 4 | $0.840 \times 10^{-3}$ |
|   | 5 | $0.820 \times 10^{-3}$ |
|   | 6 | $0.857 \times 10^{-3}$ |
|   | 7 | $0.820 \times 10^{-3}$ |
|   | 8 | $0.823 \times 10^{-3}$ |
|   | 9 | $0.856 \times 10^{-3}$ |
|   | 10 | $0.846 \times 10^{-3}$ |
| 2 | 1 | $0.940 \times 10^{-3}$ |
|   | 2 | $0.866 \times 10^{-3}$ |
|   | 3 | $0.831 \times 10^{-3}$ |
|   | 4 | $0.821 \times 10^{-3}$ |
|   | 5 | $0.813 \times 10^{-3}$ |

TABLE 1-continued

The data of the aerosol mass of two electronic cigarettes

| Sample No. | The number of smoking puffs | Aerosol mass W, g |
|---|---|---|
|   | 6 | $0.841 \times 10^{-3}$ |
|   | 7 | $0.816 \times 10^{-3}$ |
|   | 8 | $0.822 \times 10^{-3}$ |
|   | 9 | $0.851 \times 10^{-3}$ |
|   | 10 | $0.846 \times 10^{-3}$ |

With the above data, either the difference in the aerosol mass for per puff of the same electronic cigarette or the difference in the aerosol mass of different electronic cigarettes may be compared. As shown in Table 1, the aerosol mass of the electronic cigarette 1 is slightly higher than that of the electronic cigarette 2.

What is claimed is:

1. A method for evaluating an aerosol mass of an electronic cigarette, consisting of the following steps:
   (1) smoking the electronic cigarette using a Smoking Cycle Simulator to generate an aerosol, wherein the aerosol comprises a plurality of aerosol particles having a diameter range of 4 to 1000 nm;
   (2) performing a real-time measurement on the aerosol using a Fast Particulate Spectrometer comprising a charger and a classifier to obtain initial data, wherein the initial data comprises an particle size distribution of the aerosol and a particle number of the aerosol, the plurality of aerosol particles are electrified by discharge via the charger, diameters of the plurality of aerosol particles are classified via the classifier;
   (3) outputting and processing the initial data to obtain an average number concentration n corresponding to a classifying diameter $d_i$, a volume flow rate C and a testing time t, wherein the plurality of aerosol particles are classified with the classifying diameter $d_i$, the classifying diameter $d_i$ is $d_1$ to $d_{38}$ having numerical values of 4.87 nm, 5.62 nm, 6.49 nm, 7.5 nm, 8.66 nm, 10 nm, 11.55 nm, 13.34 nm, 15.4 nm, 17.78 nm, 20.54 nm, 23.71 nm, 27.38 nm, 31.62 nm, 36.52 nm, 42.17 nm, 48.7 nm, 56.23 nm, 64.94 nm, 74.99 nm, 86.6 nm, 100 nm, 115.48 nm, 133.35 nm, 153.99 nm, 177.83 nm, 205.35 nm, 237.14 nm, 273.84 nm, 316.23 nm, 365.17 nm, 421.7 nm, 486.97 nm, 562.34 nm, 649.38 nm, 749.89 nm, 865.96 nm, 1000 nm, the numerical value of the classifying diameter d is an average diameter of the aerosol particles in grade i; and
   (4) evaluating the aerosol mass according to the following formula:

$$W = \sum_{i=1}^{38} \left( \frac{1}{6}\pi d_i^3 \times \rho_0 \times 10^{-21} \times n \times \int_{t_0}^{t_1} C\,dt \right)$$

wherein W is the aerosol mass, with a unit of g; $d_i$ is the classifying diameter; $\rho_0$ is a assumed standard density of the aerosol particles, i.e., 1.0 g/cm$^3$; n is the average number concentration of the aerosol particles corresponding to the classifying diameter $d_i$, with a unit of/cm$^3$; C is the volume flow rate, with a unit of cm$^3$/s; $t_0$ is a starting testing time point, and $t_l$ is a terminal testing time point, each with a unit of s.

2. The method according to claim 1, wherein in the step (4), the aerosol mass produced by the electronic cigarette for per puff is evaluated according to the terminal testing time point $t_l$.

3. The method according to claim 1, wherein in the step (4), a sum of the aerosol mass produced by the electronic cigarette for multiple puffs is evaluated according to the terminal testing time point $t_l$.

\* \* \* \* \*